United States Patent [19]

Ramos Martinez

[11] Patent Number: 5,133,744
[45] Date of Patent: Jul. 28, 1992

[54] TUBULAR-VALUED ARTIFICIAL HEART

[76] Inventor: Wilson Ramos Martinez, Doctor Fleming, 24, Madrid, Spain

[21] Appl. No.: 461,055

[22] Filed: Jan. 4, 1990

[30] Foreign Application Priority Data

Apr. 26, 1989 [ES] Spain .................................. 8901457

[51] Int. Cl.$^5$ .............................................. A61M 1/10
[52] U.S. Cl. ........................................... 623/3; 600/16
[58] Field of Search ....................... 623/3; 600/16, 17

[56] References Cited

U.S. PATENT DOCUMENTS

| | | | |
|---|---|---|---|
| 3,733,616 | 5/1973 | Willis, Jr. | 623/3 |
| 3,955,557 | 5/1976 | Takagi | 623/3 |

FOREIGN PATENT DOCUMENTS 1388051   4/1988   U.S.S.R. .................... 623/3

OTHER PUBLICATIONS

Arterial Bypass of the Descending Thoracic Aorta with the BioMedicus Centrifugal Pump, James T. Diehl, M.D., et al., Ann Thorac Surg 44:422-423, Oct. 1987.
Fusion of prosthetic valve during left heart bypass, John L. Myers, M.D., et al., J Thorac Cardiovasc Surg 82:263-267, 1981.
Clinical temporary ventricular assist, Frederick J. Schoen, M.D., Ph.D., et al. J Thorac Cardiovasc Surg 92:1071-1081, 1986.
Early Experience with the Total Artificial Heart as a Bridge to Cardiac Transplantation, Jack G. Copeland, M.D., et al., Surgical Clinics of North America-vol. 68, No. 3, Jun. 1988, pp. 621-634.
The Total Artificial Heart as a Bridge to Transplanatation, Jack G. Copeland, M.D. et al., JAMA, Dec. 5, 1986-vol. 256, No. 21, pp. 2991-2995.
The Totally Implantable Artificial Heart: Economic, Ethical, Legal, Medical, Psychiatric, and Social Implications, A Report by the Artifical Heart and Lung Institute Jun. 1973, DHEW Publication No. (NIH) 77-191, Reprinted 1977, pp. iii-vi.

Primary Examiner—Randy C. Shay
Attorney, Agent, or Firm—Darby & Darby

[57] ABSTRACT

The artificial heart is designed for intrathoracic implantation, while its operation is effected by means of an extracorporeal control and energy feed system, form by a reduced console and interchangeable energy sectors and pneumatic sectors, also interchangeable, all of this taking up a minimum volume susceptible to being carried by the patient himself. Said heart is destined to a half life use and is based on a tubular-valved system, eliminating the classic heart chambers. The artificial heart utilizes a left sector and a right sector couplable between the left auricle and the aorta and the right auricle and pulmonary artery, respectively, sectors divided into compartments by means of cardiac valvular prostheses for the left sector and for the right sector.

9 Claims, 7 Drawing Sheets

TUBULAR-VALUED ARTIFICIAL HEART

OBJECT OF THE INVENTION

The present invention refers to an artificial mechanical heart which is based on two tubular modules which have some valves or protheses inside between which there are compartments through which the bloodstream will flow. Said two tubular valved modules determine two sectors, right and left, susceptible to operating in isolation and likewise being implanted independently as assistance or replacement pumps of the respective sectors, in failure of a human heart in difficulties.

The artificial mechanical heart is complemented by an electronic external programmable electronic controller which includes its own feed sector and an integration or reception and implementation system.

BACKGROUND OF THE INVENTION

Work on designs and modifications of an artificial mechanical heart model which has the desired feasibility has been taking place for a number of years. To said effect countless problems of all types have been come up against: technical, biocompatibility, structural, functional, unforeseen results, failures, etc., therefore it can be said that up to the moment the basic problems have not been resolved. The present models of artificial mechanical hearts present more inconveniences than benefits.

On the other hand, given the circumstances, the sue of the artificial mechanical heart has been restricted and used only as a step prior to "heart transplant", which means that its use is limited to some hours of support treatment.

Likewise the ventricular assistance pumps which are located outside the body and whose life or use is also of very few hours are used.

The known ventricular assistance pumps use two cardiac valvular prostheses which present the following problems in general:
Formation of thrombi
Extracorporeal location
Ultra-short life
Infections In connection with artificial mechanical hearts, the best known one is the one that JARVIC conceived in due time. He designed an artificial mechanical heart based on heart chambers, like the human heart, with mechanical prothesis presenting the following problems and inconveniences:
Large console
The patient is practically immobilized due to the large volume of the console
Thrombosis
Mechanical problems due to the arrangement of the design

DESCRIPTION OF THE INVENTION

The new model of artificial mechanical heart of the invention has the purpose of solving all the above-cited problems and inconveniences, being conceived to furnish the field of science with a totally novel design, based on which the multiple problems that the present models have are solved, eliminating the idea that the artificial mechanical heart is a "device" to fill a gap (for a few hours) for another type of action, for example, a heart transplant.

Likewise, the artificial heart of the invention is conceived and designed so that the patient carrying the same has it inserted in his own body, and can, within some expected logical limitations, lead a normal life, under a maintained strict system of control.

The heart in question is conceived to find a physiological solution close the original one, with all the difficulties that this involves, but taking into account the extraordinary advances in present-day technology and, above all, in the field referring to biocompatible materials, in which spectacular advances have been attained.

The control system is based on an "external programmable electronic controller" with its corresponding energy sources which control and maintain it, without requiring the large classic console as a support, as in the traditional ones, on the grounds of which the patients must be connected to a hospital bed.

Based on the new electronic controller and that its energy sources are placed on a "mini-console", the unit ends up having a reduced size and being very light which allows the patient to carry it hanging from his shoulder, with less effort and weight than the apparatus or auxiliary elements of a professional photographer.

On the other hand, the new mechanical artificial heart model is foreseen to be implanted intrathoracially, controlled, as was said, by an extracorporeal energy feed and control feed.

The basic novelty which is introduced resides ion the fact that its functionality is based on a tubular-valved system, based on which the classic heart chambers or receptacles which act as such in the known artificial hearts or systems are eliminated.

Another basic novelty consists in that, unlike the human heart and present-day artificial models, the new artificial mechanical heart includes five cardiac valvular prostheses. The tubular-valved system is divided into two sectors, a right sector and a left sector, the right and left sectors determining the normal human heart.

The function of each tubular segment is determined by the above-mentioned five cardiac valvular prostheses instead of four that the normal heart has.

In order to facilitate the system of drainage and subsequent ejection of the blood through the corresponding tubular chamber, the entire tubular-valvular system has a determined and highly physiological geometric-spatial shape, the system providing favorable circulation and the absence of ectasis in the inside of the tubes. Likewise, the indirect pneumatic action on the blood column gives a perfect physical coverage and hemodynamic functionalism to the valvular cardiac prostheses placed in the different sectors of the tubular system.

The fact that in said artificial mechanical heart which we refer to its acts passively in a phase of "admission" and of pneumatic "compression on the tubular system that contains the blood column is also outstanding. Besides it gives coverage to the system reinforcing the connections which, in turn, each carry one of the five cardiac valvular prostheses of the complete system.

Based on the design and spacial geographic arrangement, the artificial mechanical heart permits the use of biocompatible materials in the absence of the production of thromboembolic phenomena, since there are no reservoir chambers nor geometric arrangements which favor blood ectasis in any part of the tubular-valved circuit, which represents a practically unprecedented advance in this type of design.

Likewise, the new model can be used as an independent right heart implanted individually, or else as a left heart, also independent and implanted individually, or as a complete artificial mechanical heart, totally replacing the human heart.

Another service which the new artificial mechanical heart offers resides in that, based on its design a multi-programmable pacemaker which can be regulated digitally according to the patient's own needs, can be integrated, in its functionalism, in the circuit.

In its definitive or permanent intrathoracic implantation, with a closed thorax, it is housed in a sack of bovine pericardium, which practically completely isolates it from the myocardiac surface of the patient himself and from the bone structures of the anterior surface, preventing adhesions, distorsions, infections and malfunctioning of the different sectors due to their interrelationship with the structures themselves of the patient himself.

Finally, in connection with the services that the artificial heart offers, and as has already been stated, the same allows the patient to lead a normal life based on its "portable mini-console." He can maintain an acceptable quality of life and average time, completely eliminating the use for a few hours as a provisional means for a heart transplant.

As to the complete system of connections which make up the artificial mechanical heart, said system consists of six connections, three in the right sector and three in the left sector.

As to the pneumatic system, the same includes two units, one of direct action (intrathoracic) and the other of energy (extracorporeal), in such a way that the direction action unit is in turn made up of two sacs of the same material as the valved tube, with an extratubular arrangement of middle-concentric location and extension (anterior and lateral, and posterior and lateral surfaces of the tubular segment.) In other words, each tubular segment includes two sacs, the complete system of the heart comprising a total of eight sacs, two in each sector of the valved tube.

Each pneumatic sac hangs from a connection in the form of a fine tube or duct which fastens it by its middle part to the contention and protection system, where it is fastened in its external part, the admission and compression system of the pneumatic system passing through the inside thereof.

In a variant of the embodiment the pneumatic sacs of each segment form a part or body with the wall of the central valved tube, although they do not have communication with it.

The contention and protection system of the sacs and of course of the valved tubes can be said to form a slightly circular system which comprises the entire tubular-valved system and which has extensions of its structure in each connection, establishing a closed system of primary flying buttress fundamental for each connection, supporting the corresponding cardiac valvular prosthesis. It has a basic role in the pneumatic system since it carries out the static-contention phase and acts indirectly in the function of compression on the tube to produce hemodynamic ejection of the contents of the tubular-valved segment.

The entire system is isolated on the basis of an enveloping artificial sac, make of bovine pericardium so that the anterior sheet as well as the posterior sheet are sutured to the pericardium of the patient with the system installed. In this way, the mechanical artificial heart unit is totally isolated from the patient's heart surface (on its posterior surface), from the bone and sternal structures, in the anterior surface thereof, eliminating possible risks of adhesions, distorsions, infections, etc.

In connection with the electronic controller and energy sources, which have been mentioned above, it is to be noted that the system receiving said external programmable electronic controller is based on the way of operating, which may be in the following manner:

1) Synchronizing the activity of the patient's auricle through the register of the electrocardiogram and recording of the P wave of said electrocardiogram. From here, the programming is made for the functioning of the auriculoventricular activities of the artificial heart.

2) The P wave of the electrocardiogram existing, a mode of operation can be established in relation to the combined function of a multiprogrammable pacemaker with an electrode in the right auricle. In this way the function of the artificial heart can be programmed varying the parameters of the multiprogrammable pacemaker.

3) If there is no normal auricular activity, or there is a situation or irreversible auricular fibrillation, then the functioning of the cardiac cycles of the artificial heart can be determined in accordance with the pressures and volumes of auricular filling. This must be done in the operating room, when the artificial mechanical heart is implanted, since all the data of manometry will be available from the recording catheters in the different heart cavities.

In relation with the implementation of the electronic controller, it should be pointed out that said implementation is effected on the basis of a circuit integrated with the energy sector, provoking the "triggering" of the impulse towards the pneumatic sector, in such a way that in accordance with the implicit orders received it will operate measuring the pressure and frequency of action, in its double phase of admission and compression and in the auricular and ventricular sectors, of the right heart as well as of the left heart.

The external programmable controller which we are referring to also includes the corresponding connections, as well as a control board to regulate the functions.

In connection with the energy sources, it can be said that the same are divided into two parts or sectors, one called the central energy source and the other pneumatic action and energy source.

In connection with the central energy source, the same is made up of two interchangeable sectors with series arranged batteries, with an energy measuring device as well as an alarm system, when its stored energy reaches a level of 10% of the total energy, said energy source being of the atomic type, of very high voltage lithium, or any other type of energy to be determined.

In connection with the energy and pneumatic action source, it also consists of two sectors, with interchangeable individual tanks between them for drainage thereof, one to one, with an alarm system, in such a way that the interchangeability of the sectors permits there always to be one with an integral tank.

It is also convenient to mention the types of materials used, and to said effect the valved tube which is the most important noble part of the system, since it acts as heart chambers and arterial and venous vessels, the material which this is made out of can be the already known "segmented polyurethane ethicon's biomer."

A new product which excels the cited one in its basic properties, such as the absence of thromobogenesis, offering a greater elasticity and longer life, has been recently discovered and experimented on. This new material is called "THORATEC'S B.P.S.-215—M S M A COPOLYMER BLEND, hence this new material has a high stretching stress and a long life in possibilities of function, having in short the basic conditions to be used in the design of the new artificial mechanical heart.

Finally, in connection with the materials that can be used, an even newer one called "TECOFLEX" which is an aliphatic polyurethane.

In connection with the material corresponding to the connections, it should have a hardness similar to that of plastic and should be of a biocompatible nature.

The elements of contention, also called "bracelets", will be of the same biocompatible material but more elastic, since they are used to circularly reinforce the connection of the tubular system to the wings or body itself of the connections, also having a sealing system which acts under pressure and which is an adjustable type.

The coupling of the cardiac valvular prosthesis in their fastening by means of sutures to the valvular rings of the patient's heart, will be done with pressed teflon, while the cardiac valvular prothesis are preferably made entirely out of pyrolitic carbon.

The pneumatic hoses, which are two per each tubular section, must be of the same material as the valved tube itself, so that the surface pressure which is developed is not traumatic and acts by difference of pressure, directly on the tube and indirectly on the blood column, with proportional distribution of the lines of force. Each sac will cover a semi-circumferential sector.

In this way the function is made symmetric in all the points and acts minimizing the pressure by surface point, conserving the integrity of the tubular wall as well as its durability.

The auricular draining is done by cannula of the same material as that of the tubular segments, while the couplings to the aorta and pulmonary arteries will be done by tubes of a smaller caliber than the tubular segments, but of the same biocompatible material.

As to the contention and protection support of the tubular system, the material will also be of a strong consistent biocompatible material which is sufficiently malleable, in accordance with the possible changing physico-chemical conditions in order to adapt it to the geometric-spatial form that the tubular-valved system imposes.

In order to complement the description which is going to be made hereafter and for the purpose aiding a better understanding of the characteristics of the invention, the present specification is accompanied by a set of drawings in which the structural and functional features of the artificial mechanical heart of the invention will be explained in detail.

DESCRIPTION OF THE FORM OF THE PREFERRED EMBODIMENT

Figure 1:
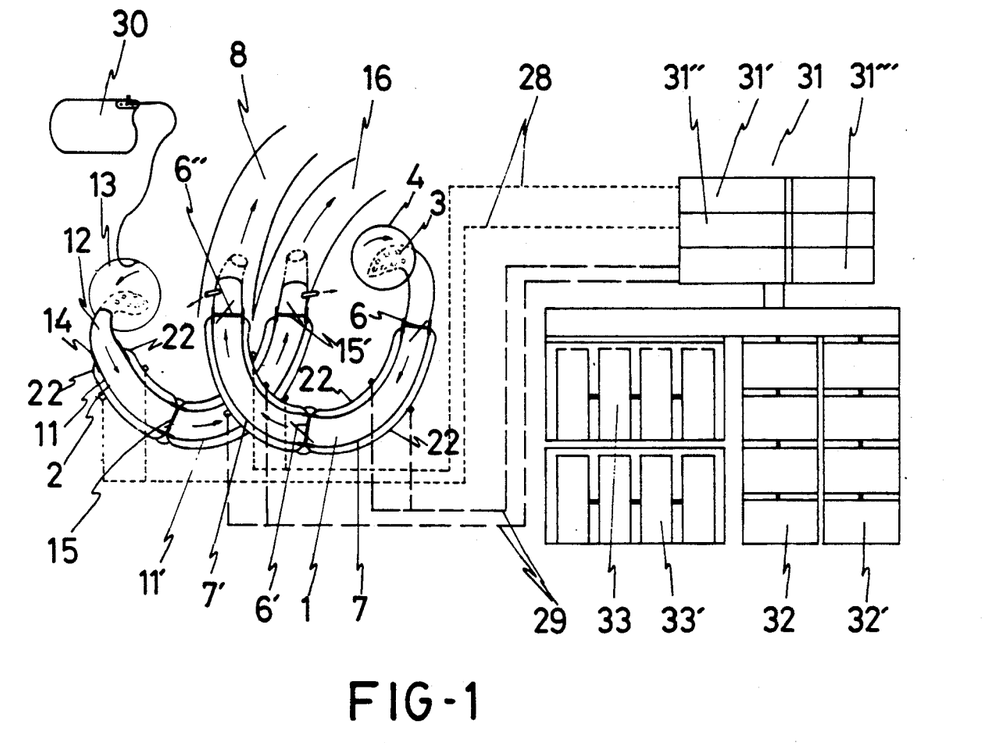
FIG. 1 is a general view, schematic plan, of the artificial heart, connected to a multiprogrammable pacemaker, as well as to the electronic controller and the corresponding energy sources thereof.

In view of these figures, and specifically mentioning FIG. 1, it can be observed how the artificial mechanical heart of the invention is based on a tubular-valved system, eliminating with this the classic heart chambers or receptacles that act as such in the conventional system. The tubular-valved system is designed to form a means of intrathoracic implantation and to be governed by a control and extracorporeal energy feed system.

Figure 2:
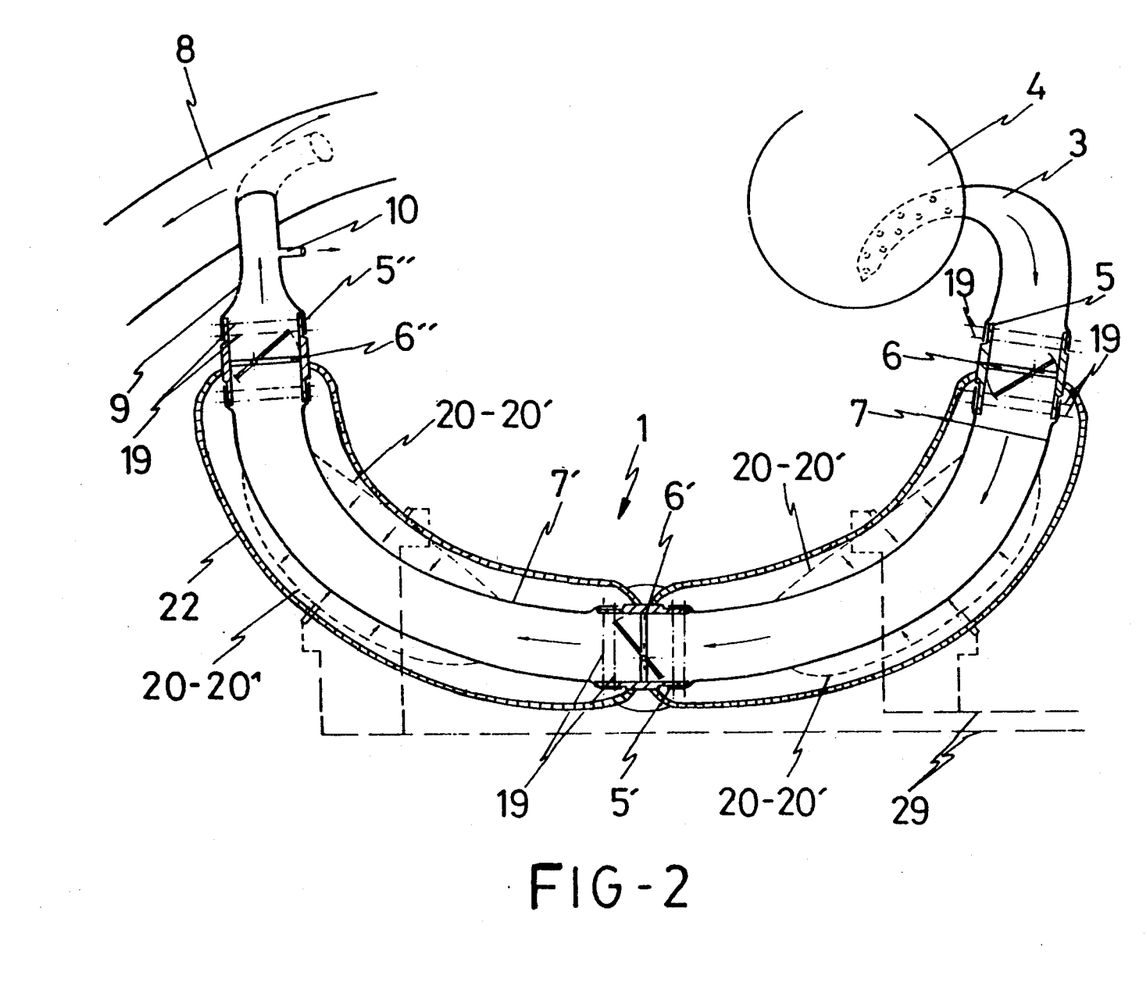
FIG. 2 shows a view with a larger detail of the left sector corresponding to the tubular-valved system which forms part of the artificial heart object of the invention.

The repeated tubular-valved system consists of two modules which determine both sectors 1 and 2 which correspond to the sectors of a natural heart. The left sector is seen to drain the blood, through a cannula 3 from the left auricle 4, and whose cannula 3 articulates by its distal end with a connection hose 5 which supports a first mitral valvular prosthesis 6 so that in the section opposite the hose 5 a segment of tube 7 which, following a curved and concave line towards the geometric center of the patient's heart, articulates and acts as a left auricular chamber. The segment 7 articulates by its distal end with a new hose 5' just as commented above and which also includes a valvular prosthesis 6'. The opposite end of said hose 5' articulates in turn the proximal end of a new tubular segment 7' which acts as a left ventricular chamber, and which in its ascending trajectory, diverted slightly to the right from the geometric center of the patient's own heart, it is directed until it reaches the ascending aorta 8. Segment 7' effects connection with the aorta through a segment 9 which is articulated to a new cap 5" to which the distal end of segment 7' articulates. Cap 5" constitutes a support for a third valvular prosthesis 6" called aortic prosthesis.

Returning to the intermediate prosthesis 6', it should be said that this is at the left heart edge of the original heart at the level of the diaphragm.

Therefore, between the left auricle 4 and the ascending aortic artery 8 module 1 formed by segments 7 and 7' which determine the left auricle and left ventricular chambers, respectively, is placed or connected. These segments 7 and 7' are connected to each other by a hose 5" which is the support of a cardiac valvular prosthesis 6', while the cited segments 7 and 7' in turn articulate the respective caps 5 and 5" which support the corresponding mitral 6 and aortic 6" valves, in order to effect the connection through said caps 5 and 5" with the left auricle itself 4 and ascending aortic artery 8, respectively.

It is convenient to point out the fact that the connection section 9 between the segment 7' and the ascending aortic artery 8 is removable. Section 9 is provided with an outlet 10 to remove air during the "priming" procedure of the system.

Figure 3:
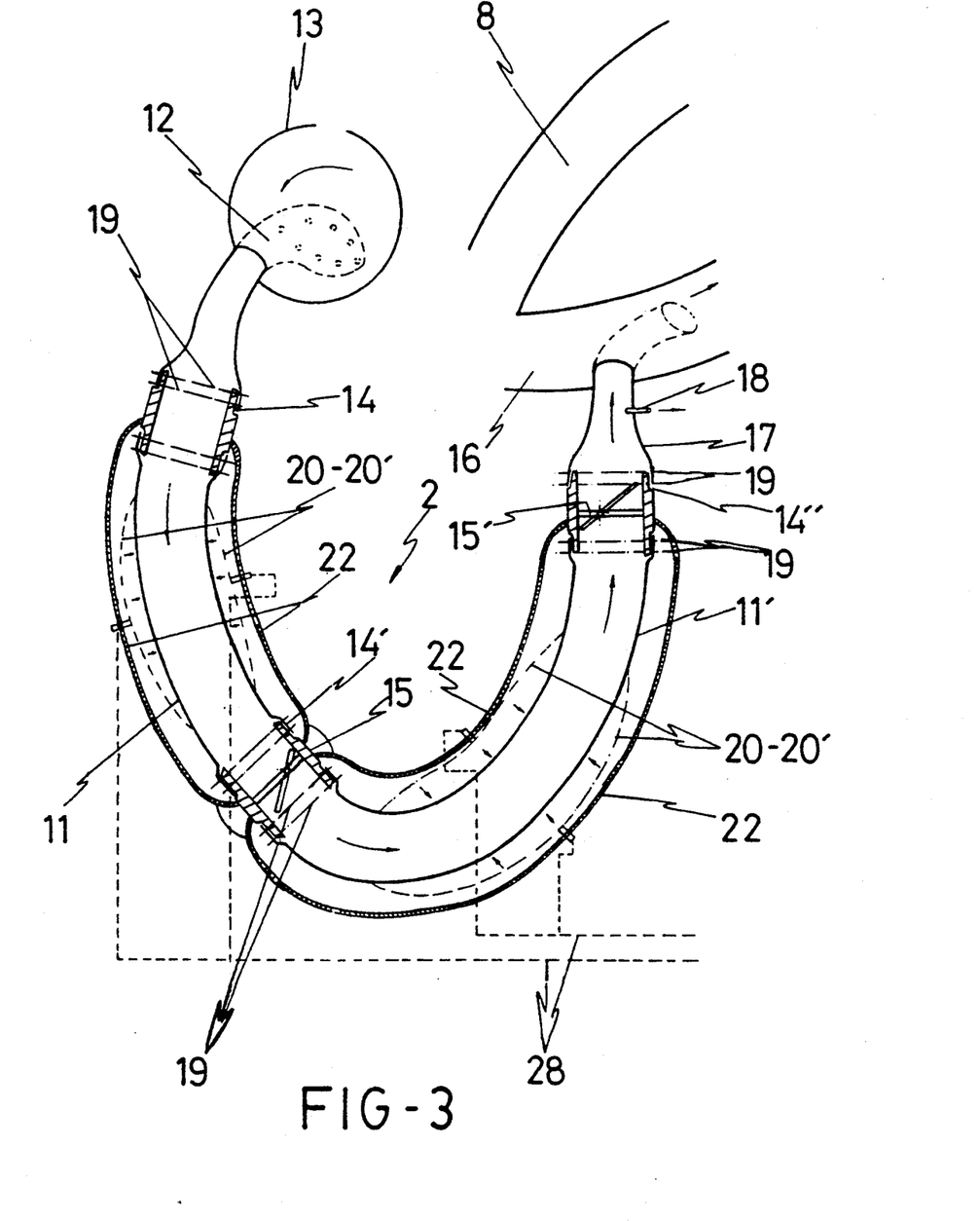
FIG. 3 shows another view also in detail of the right sector likewise corresponding to said tubular-valved system.

In connection with the module or right sector 2, the same also comprises two segments 11 and 11" which, just like the anterior ones 7 and 7', are tubes of the material which has been stated above. The segment 11 drains blood, through the corresponding cannula 12, from the right auricle 13. The distal end of this cannula 12 articulates with a connection formed by the hose 14 to which precisely one of the ends of the segment 11 is articulated, whose other end articulates with a new cap 14' which carries a tricuspid prosthesis 15. The opposite end of the cap 14' articulates with the tubular segment 11', which, at its other end, articulates with the cap 14", which is the support of a new pulmonary prosthesis 15'.

The tubular section 11 carries out the function of right auricle, so that its direction is concave towards the geometric center of the carrier's original heart, flanking the right sector of the original heart and, at the level of the diaphragm, is the connection which supports the tricuspid prosthesis 15. The tubular segment 11' runs upward and slightly towards the left of the geometric center of the patient's original heart, towards the main pulmonary artery 16. The second 17 placed between said main pulmonary artery 16 and the tubular segment 11' itself has the corresponding outlet 18 for the removal of air during the "priming" procedure of the system.

The tubular segments 7, 7', 11 and 11' should have a length and diameter so that they result in a diastolic filling of 70 cm$^3$ in order to maintain a normal heart output.

As has been seen by the description up to here, the tubular valved system comprises six connection corresponding to references 5, 5', 5", 14, 14' and 14", three corresponding to the right sector and the other three corresponding to the left sector, while the number of cardiac valvular prosthesis is five and they correspond to the references 6, 6', 6", 15, 15'.

Figure 8:
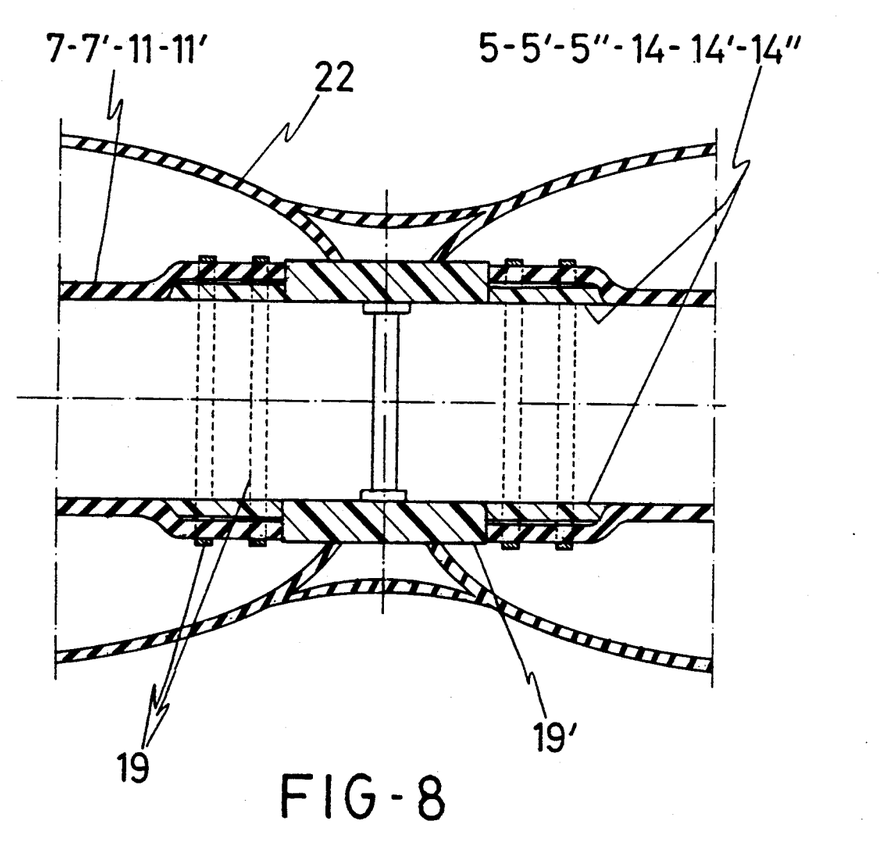
FIG. 8 shows a detailed view of the hose.

The above cited hoses are all identical and each one of them is housed under pressure upon the ends of the tubular segments which are to be connected, so that said hoses offer an internal surface which is a continuation of the surface itself corresponding to the coupled tubular segments themselves. Each connection is complemented with a pair of clamps 19 on each side, formed by five strong bands made of biocompatible material. They can be adjusted and sealed under pressure in order to obtain a perfect closing under pressure of the connection of the tubular segment itself, preventing the most minimal passing of liquid. Each connection (5, 5', 14, 14', 14") hose outside its connected hoses a radially outwardly projecting cylindric part 19' (see FIG. 8) which projects radially inwardly in the center to permit the coupling of the cardiac valvular prosthesis by means or surgical suture.

The left 1 and right 2 modules or sectors described, are completed also by a pneumatic system which includes two parts, one of direct action on said tubular segments and other extracorporeal which can be said to make up the energy part in order to feed the previously cited one.

Now then, the part that acts on the tubular segments, includes, in correspondence with each one of these segments, a pair of sacs 20 which cover, each one of them, one semicylindric part of those tubular segments.

Figures 5, 6:
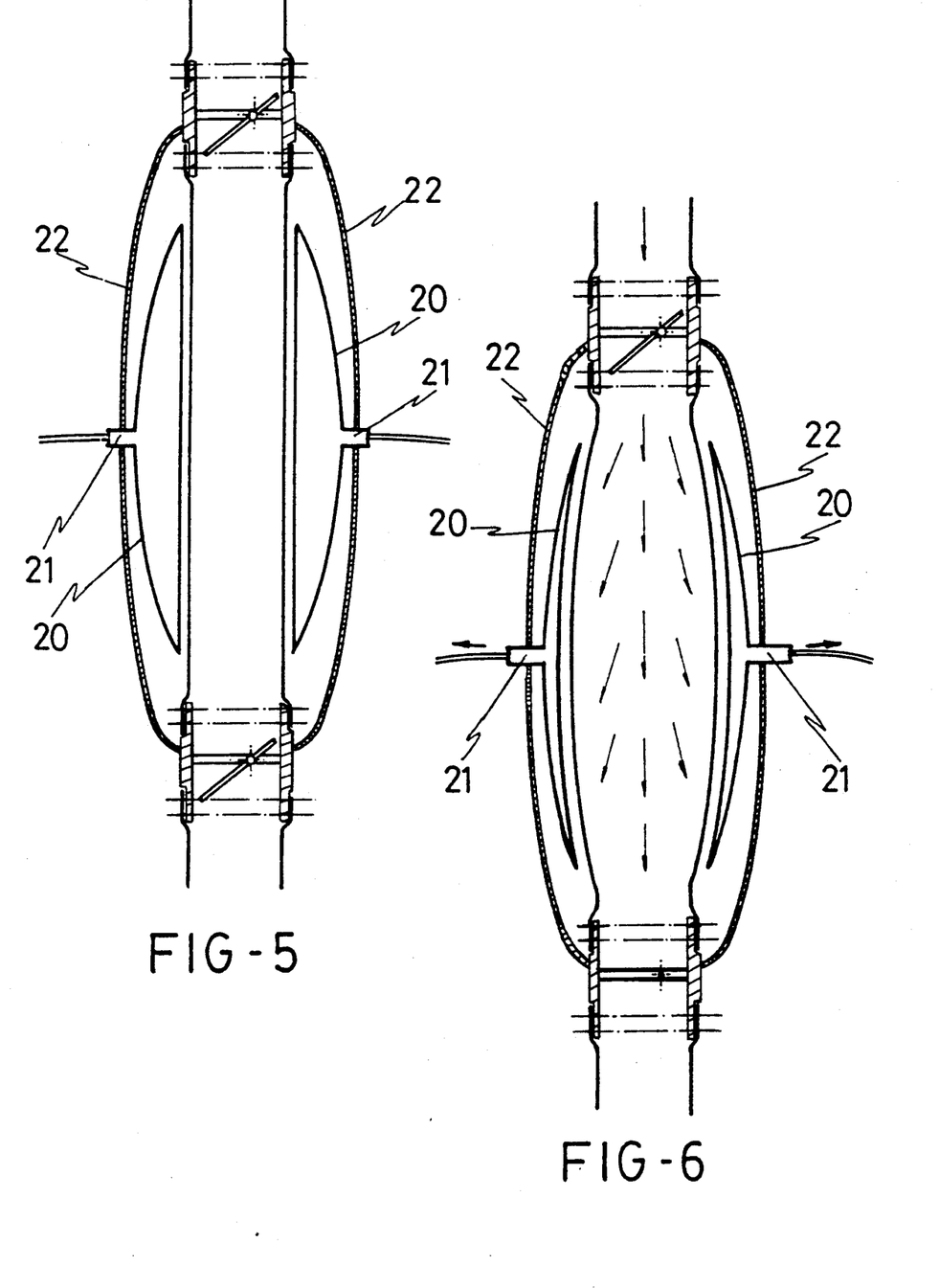
FIGS. 5, 6 and 7 show respective views of the pneumatic system in its different phases of operation, and whose system corresponds to each one of the parts or segments that are determined in the right sector as well as in the left sector of the tubular-valved system.
Figures 7, 9:
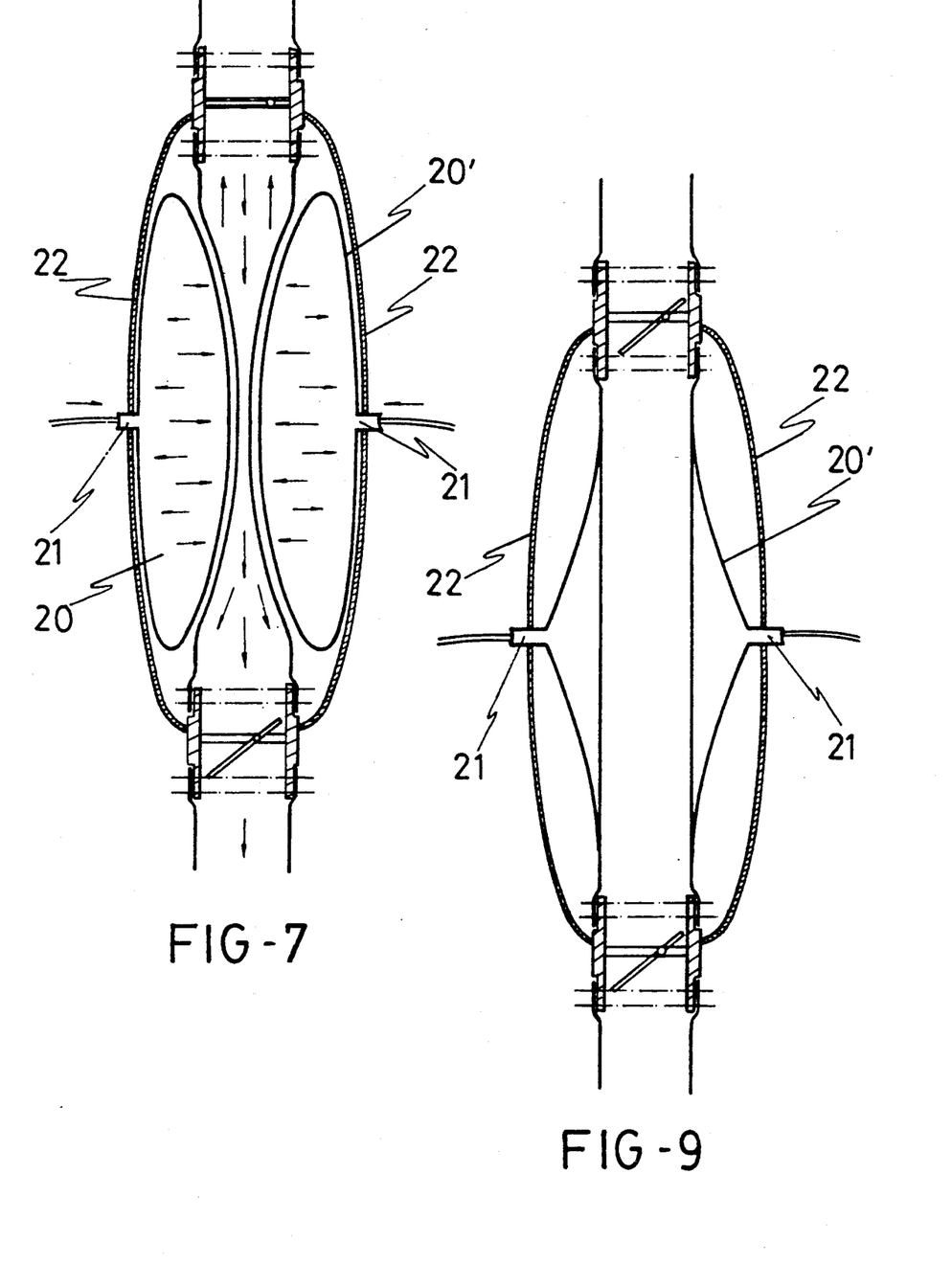
FIG. 9 shows a view similar to the one of FIG. 5, but in this case with the pneumatic sac forming part or body with the valved tube itself.

The pneumatic sacs 20 can be independent of the corresponding tubular segment, as is shown in FIGS. 5, 6 and 7, or else form part of the same tubular segment, in which case it has been given reference number 20' as has been shown in FIG. 9.

In any case both pneumatic sacs 20 or 20' are going to carry out the same function, and will be made of the same material as the corresponding tubular segment. They are situated according to a middle-concentric extension of the tubular segment, all in such a way that each pneumatic sac 20 hangs from one connection as a fine tube 21 or duct which fastens it by its middle part to a contention and protection means, where it is fastened in its outer part of the same, and through which the admission and compression system of the pneumatic system runs. The contention and protection system is made up of a very consistent wrapping which is sufficiently malleable 22, in accordance with its possibilities and changing physical or chemical conditions in order to be able to adapt it to the spatial geometric form which the tubular valved system imposes.

The contention and protection system in other words the wrapping 22 is fastened by its ends to the outside part of the corresponding valvular prosthesis.

The wrapping or contention and protection element has a main role in the operating of the pneumatic system, since it carries out the phase of static contention which acts indirectly on the function of compression on the tube to produce hemodynamic ejection of the contents of the corresponding tubular-valved segment.

Figure 4:
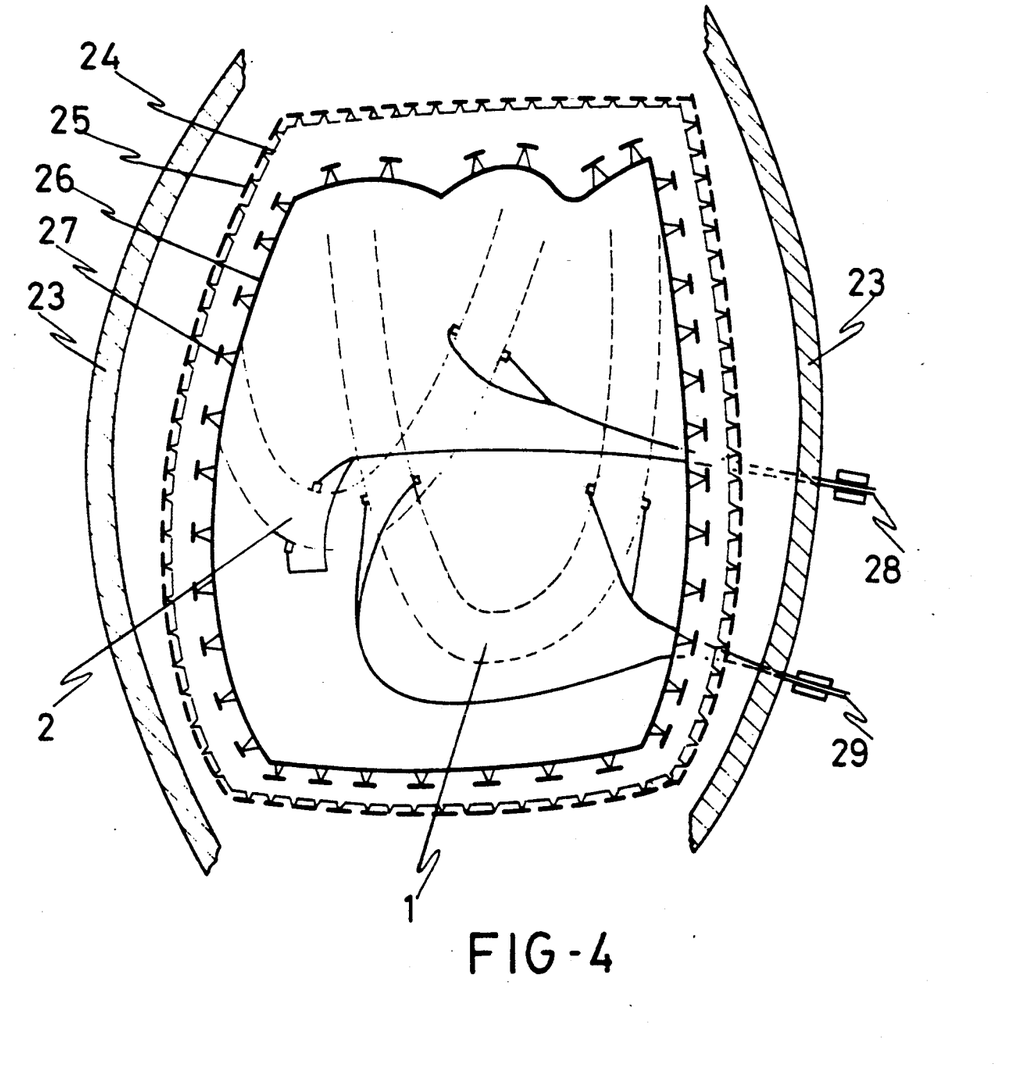
FIG. 4 shows a front view in schematic plan of the arrangement of the tubular-valved system which forms part of the artificial heart of the invention; located intrathoracically in a patient, with the external enveloping protection of the unit, and in section the thoracic cavity of said patient.

In FIG. 4 one can see the system in thoracic implantation, observing in section the patient's thoracic cavity open and referred to with number 23, inside of which the described artificial heart is implanted, in other words, the part corresponding to the tubular-valved system with its corresponding direct action pneumatic system, all housed in the inside of the human pericardium.

In FIG. 4 one can see how said system or artificial mechanical heart is protected by an enveloping pericardium of bovine material, whose posterior sheet 24 is fastened by suture 25 to the human pericardium, while the anterior sheet 26 of the artificial pericardium is fastened to the human pericardium by means of suture 27. The external connections 28 and 29 for the energy supply has likewise been schematically represented in FIG. 4.

On the other hand, it can be said that the system implanted in a patient can be complemented by a multi-programmable pacemaker 30, connected to the right auricle 13. The function of the artificial heart can be programmed by simply varying the parameters of the pacemaker 30.

In connection with external programmable electronic controller, the same is based on a small console 31 which includes sectors 31', 31" and 31"', right as well as left, corresponding to controls, general as well as energy and pneumatic controls, console which is associated to the corresponding energy sectors 32 and 32', independent and interchangeable between each other, and to the pneumatic sectors 33 and 33', which are also interchangeable between each other.

In accordance with all of the above it is obvious that the modules or sectors 1 and 2 of the artificial heart itself represent the left and right sectors of the normal human heart, so that the blood drains gravitationally from the left auricle 4 of the patient to the tubular-valvular system or segment 7 which is the left auricle itself. The action of pneumatic "admission" of said segment 7 aids this gravitational action as is represented clearly in FIGS. 5, 6 and 7, and even in FIG. 8.

Therefore, the blood column coming from the left auricle 4 will open the first mitral prosthesis 6 and will begin to fill the reservoir of the tubular segment 7 until the pressure in it suffices to produce the opening of the second prosthesis 6', then the pneumatic compression phase acts, just as is represented in FIG. 7, doing so in a doubly beneficial manner, since on the one hand it will make the first mitral prosthesis 6 close, thus avoiding blood reflux towards the valved sector of the left auricle of the patient himself and of the pulmonary veins, and on the other hand it will reinforce auricle systole, opening the second mitral prosthesis which, in its final phase of compression makes this prosthesis close and said blood column passes entirely to the following tubular segment 7', the latter acting as the left ventricle.

After a pre-established pause, the pneumatic compressor corresponding to the tubular chamber of segment 7' which acts as a left ventricle, and the blood, driven by said force, comes out towards the patient's ascending aorta, previously opening the aortic prosthesis 6" which is found in the preterminal end of the tubular segment 7', in other words, between that end and the section 9 coupled to said aorta 8.

When the systole stops, the aortic prosthesis referred to in the last place, in other words 6" closes. The described heart cycle begins again.

It is necessary to allude to the fact that in said left sector 1 two mitral prostheses instead of one which is normal and which is normal in the normal human heart have been implanted, and this implantation of two mitral prosthesis 6 and 6' is due to the following:

a) Because it makes it possible to operate with a shortening or lengthening of the left auricular filling period b) Because pulmonary hypertension is reduced to avoid left auricular reflux.

c) Because the occurrence or production of a possible clinical-hemodynamic picture of "acute pulmonary edema" is almost completely eliminated.

d) Because the pre-charge acts at will.

e) Because the artificial heart rate is regulated over the true or original one of the patient himself.

f) Because a complete by-pass is made of the left sector, leaving the pulmonary vascular sector and left ventricle to rest sufficiently, obtaining an absence of alterations in the gaseous interphase at the pulmonary level, therefore, forming an almost perfect cardiopulmonary function.

On its part, the right sector 2 manages to drain the blood form the right auricle 13, drainage which is gravitational and aided by the admission system which makes the blood column press on the opening of the tricuspid valvular prosthesis 15.

When the tubular sector 11' which acts as a right ventricle has acquired the auricular volume, the blood column itself causes the closing of the tricuspid valvular cardiac prosthesis 15, at which time the pneumatic compression system of the tubular sector 11', which acts as right ventricle is activated, generating a systolic impulse which opens the pulmonary prosthesis 15' and distributes the blood through the main pulmonary artery 16 and its branches, for pulmonary circulation, where the hematosis is carried out and the blood returns oxygenated to the sector of the left auricle, in such a way that once this is finished the cycle is restarted again.

The triggering of the start of the cardiac cycle, according to the described artificial mechanical heart or system is carried out as follows:

Upon the entire described system being connected to the corresponding electronic controller, which is outside the patient himself, the corresponding controls make it possible to activate the pneumatic system for the triggering thereof, in time and admission pressure and gaseous compression pressure for each section of the respective sector.

Therefore, the cycle can be started in various ways, in other words:

1) If the patient with the artificial mechanical heart has normal auricular activity of his own, in other words, that the P wave can be registered in his electrocardiogram, then an electrode can be implanted in the right auricle and connected to a generator of a multiprogrammable pacemaker system, as is shown in FIG. 1. In this way, with the signal of the P wave of the patient's electrode, the artificial cardiac cycle can be programmed with the desired parameters.

2) If the patient does not have his own normal auricular activity, for example, if there is "maintained and irreversible auricular fibrillation," then the artificial cardiac cycle can be regulated in accordance with the pressures of the auricular sectors, right as well as left, and their filling volumes. This can be done with total safety and efficiency in the operating room, when the cited artificial mechanical heart is implanted with all the necessary manometric data that the intracavitary catheters provided in the different heart chambers provide, regulating the operation and processing the new program of the artificial heart cycle.

As has been seen throughout the present description, the tubular-valved artificial mechanical heart, of intrathoracic implantation, avoids the classic heart chambers which the conventional systems use, permitting the patient to lead a normal life, on the basis of which the entire system of the external programmable electronic controller, with said energy sources, constitute a portable mini-console which takes up very little space which can be transported without any problem by the user, without much volume being taken up.

On the other hand, due to its special geometric-spatial shape, the hemodynamic function and the functioning of the prothesic systems are undoubtedly favored, making the functioning thereof highly physiological and close to reality. The hemodynamic function is also enhanced on the basis of two mitral prostheses which the left tubular sector or module has.

It has also been commented that the system may be used as a complete artificial mechanical heart, totally replacing the human heart, or else it can be used as an independent right heart implanted individually or else as a left heart, also independent and implanted individually.

I claim:

1. An artificial heart for a patient comprising:
   a first flexible tubular sector for receiving blood, said first tubular sector having at one end means for coupling to the left auricle and having at the other end means for coupling to the ascending aorta;
   a plurality of first valve means positioned within said first tubular sector;
   a second flexible tubular sector for receiving blood, said second tubular sector having at one end means for coupling to the right auricle and having at the other end means for coupling to the main pulmonary artery;

a plurality of second valve means positioned within said second tubular sector; and pneumatic means for receiving gas surrounding a portion of said first and second tubular sectors, said pneumatic means pressing against said first and second tubular sectors in response to reception of the gas so as to compress said first and second tubular sectors thereby pushing the blood in said first and second sectors against at least one of said plurality of first valve means and plurality of second valve means to open said at least one of said plurality of first and second valve means, the pressure in said first and second sectors closing at least one of said plurality of first and second valve means, whereby the flow of blood is controlled through said first and second tubular sectors.

2. An artificial heart of claim 1, wherein said plurality of first valve means comprises a first valve positioned at said one end of said first tubular sector, a second valve positioned at said other end of said first tubular sector and a third valve positioned between said one and other ends of said first tubular sector and wherein said plurality of second valve means comprises a fourth valve positioned at said one end of said second tubular sector and a fifth valve positioned between said one end and the other end of said second tubular sector.

3. An artificial heart according to claim 2, wherein said pneumatic means surrounding said sectors comprises two pairs of pneumatic sacs, the first pair of pneumatic sacs having one pneumatic sac positioned between said first and third valves and a second pneumatic sac positioned between said second and third valves and the second pair of pneumatic sacs having one pneumatic sac positioned between said fourth and fifth valves and a second pneumatic sac positioned between said fifth valve and the means for connecting to main pulmonary artery.

4. An artificial heart in accordance with claim 3 further comprising protective wrappings enveloping said tubular sectors and said penumatic sacs.

5. An artificial heart in accordance with claim 4 wherein said pneumatic sacs include tubes extending through said protective wrappings for receiving externally applied gas.

6. An artificial heart according to claim 3 in which said pneumatic sacs are parts of the respective tubular sector, thereby forming a chamber between the outer surface of the respective sector and the wall of said pneumatic sac.

7. An artificial heart according to claim 1 in which said first and second tubular sectors are enclosed in an artificial sac, said artificial sac having an anterior sheet and a posterior sheet and said sheets being adapted to be fastened by means of sutures to the pericardium of the patient.

8. An artificial heart according to claim 1, wherein said first and second tubular sectors and said pneumatic sacs are formed of biocompatible materials.

9. An artificial heart according to claim 1, wherein said means for coupling to said left auricle is a cannula, said means for coupling to said aorta is a first hose, said means for coupling to said right auricle is a cannula and said means for coupling to said pulmonary artery is a second hose.

* * * * *